United States Patent
Gerber

(10) Patent No.: US 10,258,728 B2
(45) Date of Patent: Apr. 16, 2019

(54) SELECTIVE SORBENT-BASED REGENERATION DIALYSIS SYSTEMS AND METHODS

(71) Applicant: Medtronic, Inc., Minneapolis, MN (US)

(72) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 204 days.

(21) Appl. No.: 15/265,001

(22) Filed: Sep. 14, 2016

(65) Prior Publication Data

US 2017/0087291 A1  Mar. 30, 2017

Related U.S. Application Data

(60) Provisional application No. 62/232,541, filed on Sep. 25, 2015.

(51) Int. Cl.
*A61M 1/16* (2006.01)
*A61M 1/26* (2006.01)
*A61M 39/22* (2006.01)

(52) U.S. Cl.
CPC ........ *A61M 1/1696* (2013.01); *A61M 1/1603* (2014.02); *A61M 1/1609* (2014.02); *A61M 1/267* (2014.02); *A61M 39/22* (2013.01); *A61M 2205/3317* (2013.01);
(Continued)

(58) Field of Classification Search
CPC .. A61M 1/1696; A61M 1/1656; A61M 1/287; A61M 2205/3334; A61M 1/165; A61M 1/1654; A61M 1/1672; A61M 1/3679
See application file for complete search history.

(56) References Cited

U.S. PATENT DOCUMENTS

| 8,580,112 B2 | 11/2013 | Updyke |
| 2002/0023879 A1* | 2/2002 | Hadden ................. A61M 1/16 210/646 |
| 2005/0131332 A1 | 6/2005 | Kelly |

(Continued)

FOREIGN PATENT DOCUMENTS

| JP | 2006325668 A | 12/2006 |
| WO | 2011113572 A1 | 9/2011 |
| WO | 2012138604 A2 | 10/2012 |

OTHER PUBLICATIONS

[NPL697] International Search Report from International Application No. PCT/US2016/051668, dated Dec. 8, 2016.
(Continued)

*Primary Examiner* — Ana M Fortuna
(74) *Attorney, Agent, or Firm* — Kenneth Collier; Roger Hahn

(57) ABSTRACT

Systems and methods are provided for performing selective sorbent-based regeneration of dialysate. The systems and method provide for dialysate regeneration to be carried out intermittently throughout a dialysis session, decreasing the necessary amounts of sorbent materials and infusates to conduct dialysis. The system and methods allow for regeneration of dialysate as needed based on the concentration of waste species in the dialysate, allowing for effective treatment with a decreased need for sorbent materials.

28 Claims, 8 Drawing Sheets

(52) U.S. Cl.
CPC ... *A61M 2230/005* (2013.01); *A61M 2230/20* (2013.01); *A61M 2230/65* (2013.01)

(56) References Cited

U.S. PATENT DOCUMENTS

| | | | |
|---|---|---|---|
| 2005/0274659 A1* | 12/2005 | Hsu | C02F 9/005 210/109 |
| 2011/0272337 A1 | 11/2011 | Palmer | |
| 2013/0274642 A1* | 10/2013 | Soykan | A61M 1/28 604/5.01 |
| 2014/0021111 A1* | 1/2014 | Roger | A61M 1/14 210/96.2 |
| 2014/0190886 A1 | 7/2014 | Pudil | |
| 2014/0217029 A1 | 8/2014 | Meyer | |

OTHER PUBLICATIONS

[NPL698] Written Opinion from International Application No. PCT/US2016/051668, dated Dec. 8, 2016.
International Search Report from International Application No. PCT/US2016/051668, dated Dec. 8, 2016.
Written Opinion from International Application No. PCT/US2016/051668, dated Dec. 8, 2016.

* cited by examiner

SELECTIVE SORBENT-BASED REGENERATION DIALYSIS SYSTEMS AND METHODS

CROSS-REFERENCE TO RELATED APPLICATIONS

This application claims the benefit of and priority to U.S. Provisional Patent Application No. 62/232,541 filed Sep. 25, 2015, the entire disclosure of which is incorporated by reference herein.

FIELD OF THE INVENTION

The invention relates to dialysis systems and methods for carrying out sorbent-based regeneration cooperating with dialyzer flow loops. The system and methods provide for selective regeneration of dialysate in a sorbent dialysis system by passing the dialysate through a dialyzer multiple times without regenerating the dialysate and then selectively passing the spent dialysate through a sorbent cartridge. The system and methods provide for both effective dialysis treatment and efficient use of sorbent materials.

BACKGROUND

Sorbent cartridges operate by adsorbing ions and other waste solutes from a fluid, such as dialysate. In addition to removing wastes, such as urea, phosphates and non-polar molecules, sorbent cartridges can also remove non-waste ions from the dialysate, such as potassium, calcium and magnesium. Certain common sorbent materials, such as zirconium oxide and zirconium phosphate are expensive. Removal of both wastes and non-waste components from dialysate results in a need for a large amount of these expensive sorbent materials, raising the costs of sorbent dialysis.

To avoid the use of sorbent based regeneration, some systems recirculate dialysate back to a patient multiple times. One such dialysis system is described in U.S. Pat. No. 8,034,017. The known system is intended for at-home, nocturnal use, and includes a dialyzer and two containers along with pumps to regulate flow into the dialyzer. The system operates by circulating dialysate from the containers to the dialyzer and back into the containers. The system has no sorbent cartridge system to remove contaminants in the dialysate, and instead relies on a large starting volume of 10-20 L to provide sufficient buffering and dilution capacity throughout a therapy session. However, the level of contaminants introduced from the spent dialysis can be significant enough to affect therapy. Although a dialysate flow rate can be reduced to use a smaller volume of dialysate, a lower flow rate also reduces the flux rate of contaminants across the dialyzer membrane, thereby increasing the necessary dialysis time. Further, the system cannot add substances or regulate electrolyte or pH levels during operation.

Although the cost of water is generally less than the cost of sorbent materials, dialysis systems that reuse spent dialysate require a relatively large amount of clean source water to use in generating the dialysate. In many parts of the world, large amounts of pure water are not readily available. In contrast, use of a sorbent cartridge in order to remove wastes from dialysate during dialysis can allow for a dialysis session with significantly less clean water. Because the patient's wastes are removed from the dialysate, the dialysate can be recirculated back to the dialyzer without the need for disposal. Use of a sorbent cartridge also reduces the amount of source water to which the patient is exposed. Source water may contain certain contaminants, and exposing the patient to less source water can reduce the amount of these contaminants to which the patient is exposed.

As such, a system is needed to eliminate the problems associated with reusing spent dialysate without full regeneration of the spent dialysate in a cost-effective manner. There is a need for a system that can provide a dual system of passing dialysis multiple times through a dialyzer that cooperates with a sorbent based regeneration system to selectively regenerate dialysate at a desired time or condition. The system should be able to regenerate dialysate selectively, intermittently, and on-demand. The systems should allow for the use a smaller amount of sorbent material and a shorter dialysis time than described in known prior art, such as the standard 2-4 hour dialysis sessions. There is also a need for a system that can reduce the amount of sorbent materials necessary for carrying out sorbent dialysis without increasing the amount of clean water required. There is further a need for systems and methods that allow for regeneration of dialysate less often during a dialysis session, thereby lowering the sorbent material requirements while maintaining effective treatment of dialysis patients.

SUMMARY OF THE INVENTION

The first aspect of the invention relates to a dialysis flow loop. In any embodiment of the first aspect of the invention, the dialysis flow loop can comprise a dialyzer flow loop comprising a dialyzer and at least one dialysate storage container, a regeneration flow loop fluidly connected to the dialyzer flow loop and comprising a sorbent cartridge, at least one valve positioned to control fluid movement between the dialyzer flow loop and the regeneration flow loop; and a controller to control the valve, wherein the controller controls the valve based on an amount of waste solutes in a dialysate in the dialyzer flow loop.

In any embodiment of the first aspect of the invention, the dialysis flow loop can comprise at least a first dialyzer flow loop pump located in the dialyzer flow loop, and at least one regeneration flow loop pump located in the regeneration flow loop.

In any embodiment of the first aspect of the invention, the dialysis flow loop can comprise a second dialyzer flow loop pump, wherein the first dialyzer flow loop pump is located on an inlet side of the dialyzer, and wherein the second dialyzer flow loop pump is located on an outlet side of the dialyzer.

In any embodiment of the first aspect of the invention, the dialysis flow loop can comprise a second dialysate storage container in the dialyzer flow loop; wherein the first dialysate storage container is located on an inlet side of the dialyzer, and wherein the second dialysate storage container is located on an outlet side of the dialyzer.

In any embodiment of the first aspect of the invention, the dialysis flow loop can comprise a dialysate storage container in the regeneration flow loop at a position downstream of the sorbent cartridge.

In any embodiment of the first aspect of the invention, the controller can switch the valve between a dialysis mode and a regeneration mode, wherein fluid does not enter the regeneration flow loop from the dialyzer flow loop in the dialysis mode, and wherein fluid does enter the regeneration flow loop from the dialyzer flow loop in the regeneration mode.

In any embodiment of the first aspect of the invention, fluid exiting the dialyzer can enter the second dialysate storage container.

In any embodiment of the first aspect of the invention, fluid exiting the first dialysate storage container can enter the dialyzer.

In any embodiment of the first aspect of the invention, one or both of the dialysate storage containers can have a volume of between any of 0.5 L to 7 L, 0.5 L to 1 L, 0.5 L to 2 L, 1 L to 2 L, 2 L to 5 L or 5 L to 7 L.

In any embodiment of the first aspect of the invention, the regeneration flow loop can comprise an infusate system.

In any embodiment of the first aspect of the invention, the dialysis flow loop can comprise a first flow sensor on the inlet side of the dialyzer and downstream of the first dialysate storage container, and a second flow sensor on the outlet side of the dialyzer and upstream of the second dialysate storage container.

In any embodiment of the first aspect of the invention, the dialysis flow loop can comprise a first dialyzer flow loop pump located on the inlet side of the dialyzer downstream of the first dialysate storage container; and a second dialyzer flow loop pump located on the outlet side of the dialyzer upstream of the second dialysate storage container.

In any embodiment of the first aspect of the invention, the dialysis flow loop can comprise an analyte sensor positioned in the dialyzer flow loop, the analyte sensor in electronic communication with the controller.

In any embodiment of the first aspect of the invention, the analyte sensor can be a urea sensor or a conductivity sensor.

Any of the features disclosed as being part of the first aspect of the invention can be included in the first aspect of the invention, either alone or in combination.

The second aspect of the invention is drawn to a method. In any embodiment of the second aspect of the invention, the method can comprise initiating dialysis with dialysate initially located in a first dialysate storage container positioned in a dialyzer flow loop; passing the dialysate through a dialyzer and into a second dialysate storage container positioned in the dialyzer flow loop; and moving the dialysate in the second dialysate storage container into the first dialysate storage container.

In any embodiment of the second aspect of the invention, the dialysate can be moved from the second storage container to the first storage container when the first storage container is empty.

In any embodiment of the second aspect of the invention, the method can comprise selectively moving the dialysate from the second dialysate storage container into a regeneration flow loop, wherein the regeneration flow loop comprises a sorbent cartridge; passing the dialysate through the sorbent cartridge to create a regenerated dialysate, and then moving the regenerated dialysate from the regeneration flow loop to the first storage container.

In any embodiment of the second aspect of the invention, the regenerated dialysate can be stored in a third storage container prior to moving the regenerated dialysate to the first storage container.

In any embodiment of the second aspect of the invention, the amount of dialysate initially present in the first dialysate storage container can be between any of 0.5 L to 7 L, 0.5 L to 1 L, 0.5 L to 2 L, 1 L to 2 L, 2 L to 5 L or 5 L to 7 L.

In any embodiment of the second aspect of the invention, the method can comprise the step of preparing a dialysate prior to initiating the dialysis session; wherein preparing the dialysate comprises: moving water from a water source into the regeneration flow loop; passing the water through the sorbent cartridge; adding one or more infusates to the water to create a dialysate; and moving the dialysate from the regeneration flow loop into the first storage container.

In any embodiment of the first aspect of the invention, the regenerated dialysate can be stored in the third dialysate storage container for less than one hour prior to moving the regenerated dialysate to the first storage container.

In any embodiment of the first aspect of the invention, the dialysate can be moved from the second dialysate storage container into the regeneration flow loop any of every 1-60 minutes, every 1-20 minutes, every 1-7 minutes, every 5-10 minutes, every 7-12 minutes, every 5-15 minutes, every 10-15 minutes, every 12-20 minutes, every 15-30 minutes, every 20-45 minutes, every 30-40 minutes, every 40-60 minutes or every 40-50 minutes.

In any embodiment of the second aspect of the invention, dialysate can be moved into the regeneration flow loop based on an amount of waste solutes in the dialysate.

In any embodiment of the second aspect of the invention, a second volume of dialysate can be moved from a third dialysate storage container positioned in the regeneration flow loop to the first dialysate storage container when dialysate from the second storage container is moved to the regeneration flow loop.

In any embodiment of the second aspect of the invention, a flow rate of dialysate in the dialyzer flow loop can be faster than a flow rate of dialysate in the regeneration flow loop.

In any embodiment of the second aspect of the invention, the flow rate of dialysate in the dialyzer flow loop can be between any of 1-10, 1-2, 1-4, 2-4, 3-5, 3-8, 5-7, or 7-10 times the flow rate of dialysate in the regeneration flow loop.

In any embodiment of the second aspect of the invention, dialysate is moved into the regeneration flow loop based on a timing within a dialysis session.

In any embodiment of the second aspect of the invention, dialysate can be moved into the regeneration flow loop more frequently at a later point in the dialysis session than at an earlier point in the dialysis session.

In any embodiment of the first or second aspects of the invention, the dialysate initially located in the first dialysate storage container can be disposed of and may not be regenerated.

Any of the features disclosed as being part of the second aspect of the invention can be included in the second aspect of the invention, either alone or in combination.

DETAILED DESCRIPTION OF THE INVENTION

Figure 1:
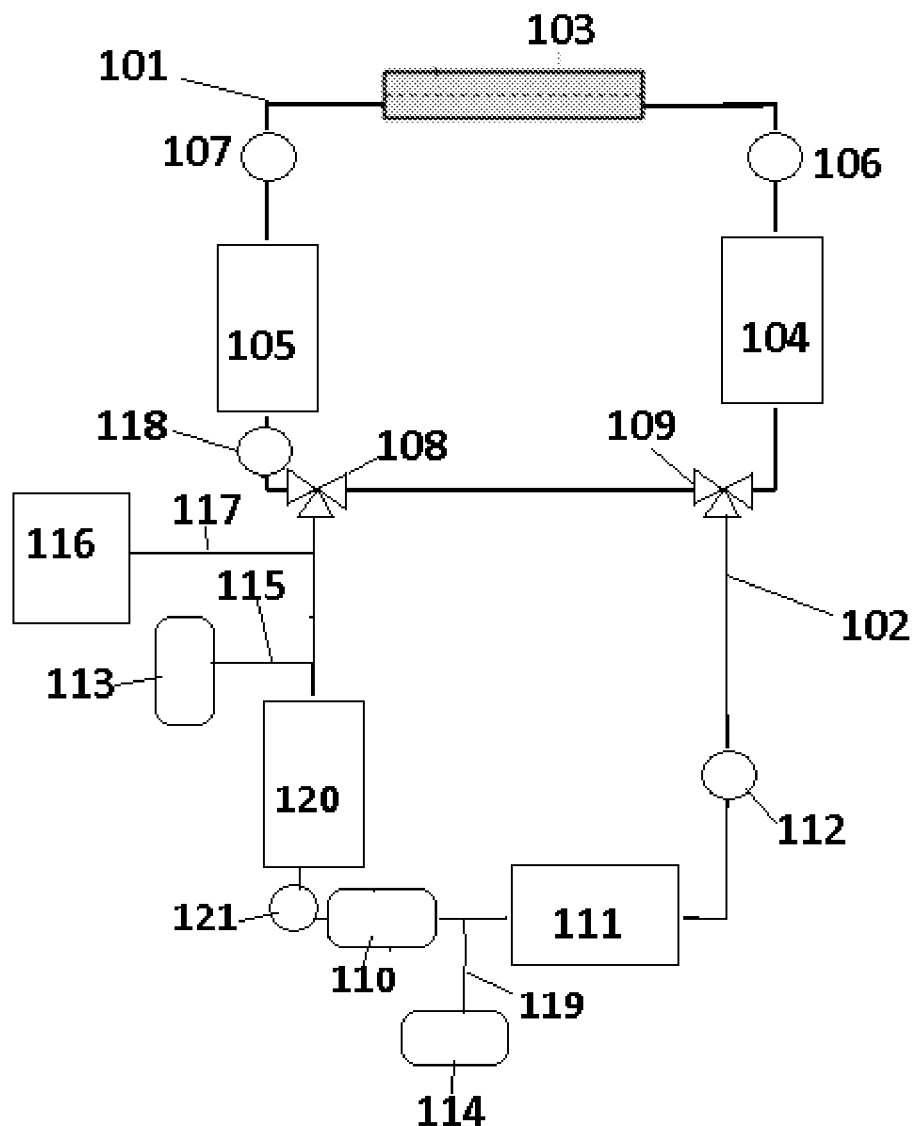
FIG. 1 shows a dialysis flow loop for use in selective sorbent-based regeneration of dialysate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "amount of waste solutes" refers to the concentration of one or more waste solutes in a fluid.

An "analyte sensor" is a sensor capable of determining, either directly or indirectly, the concentration of one or more solutes in a fluid.

The term "blood urea nitrogen (BUN)" refers to a measurement of the total amount of nitrogen in the blood of a patient that comes from urea. The BUN measurement is generally given in units of mg/dl.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "container" is a receptacle that may be flexible or inflexible for holding any fluid or solid, such as a spent dialysate fluid, or a sodium chloride or sodium bicarbonate solution or solid, or urease, or urease/alumina.

The term "control fluid movement" refers to the ability of a component to determine the direction of fluid flow, or to determine whether or not fluid will flow through a particular point in the system.

A "controller," "control unit," or "processor" is any device which monitors and affects the operational conditions of a given system. The operational conditions are typically referred to as output variables of the system wherein the output variables can be affected by adjusting certain input variables.

The term "dialysate" describes a fluid into or out of which solutes from a fluid to be dialyzed diffuse through a membrane. A dialysate typically contains electrolytes that are close in concentration to the physiological concentration of electrolytes found in blood. A common sodium level for dialysate is approximately 140 mEq/L. Normal blood sodium levels range from approximately 135 mEq/L to 145 mEq/L. The REDY system typically uses dialysate ranging from 120 mEq/L to 160 mEq/L.

A "dialysate storage container" is any container configured to contain dialysate for use in dialysis. The dialysate in the dialysate storage container can be newly prepared dialysate, regenerated dialysate, or used dialysate.

A "dialysate storage flow loop" is a route that fluid can travel during dialysis, wherein the fluid travelling in the dialyzer storage flow loop can be held until needed for regeneration or use of the fluid.

A "dialysate storage flow loop pump" is a pump positioned to move fluid through, into or out of a dialysate storage flow loop.

"Dialysis" or "dialysis therapy" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis flow path" or "dialysis flow loop" is the route in which a fluid will travel during dialysis.

The term "dialysis mode" refers to a mode of operation of a dialysis system wherein dialysis can take place.

The term "dialysis session" refers to a course of treatment of a patient by dialysis.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly (methyl methacrylate), modified cellulose, or other materials known to those skilled in the art.

A "dialyzer flow loop" is a route that fluid can travel during dialysis, wherein the fluid travelling in the dialyzer flow loop will pass through a dialyzer.

A "dialyzer flow loop pump" is a pump positioned to move fluid through, into or out of a dialyzer flow loop.

The term "disposed of" refers to the process of removing a material from a system without the intention to reintroduce the material back into the system. The term is not limited to complete removal of the material, and may be used to refer to the movement of the material into a waste container or other container for later disposal.

"Downstream" refers to the respective positions of two components or positions in a dialysis flow loop. Fluid moving in the dialysis flow loop will contact a downstream component or position after contacting an upstream component or position.

The term "earlier point in time" refers to a point in time that occurs before some other "later point in time."

"Electronic communication" refers to the connection between the electrical elements of the system, either directly or wirelessly.

"Flow" refers to the movement of a fluid or gas.

The term "flow rate" refers to the amount of fluid moving passed a particular point per unit of time.

A "flow sensor" is a sensor that can measure the rate of flow at a particular point within a dialysis system.

A "fluid" is a liquid substance optionally having a combination of gas and liquid phases in the fluid. Notably, a liquid can therefore also have a mixture of gas and liquid phases of matter.

The term "fluid connection," "fluidly connectable," "fluidly connected," or "fluid connector" refers to the ability to pass fluid or gas from one point to another point. The two points can be within or between any one or more of compartments, modules, systems, components, and rechargers, all of any type.

The term "infusate container" refers to a source from which infusates can be obtained. Examples of infusates include, but are not limited to, calcium, magnesium and potassium. The source can be a solution containing infusates or dry compositions that are hydrated by the system. The infusate container is not limited to cations and may optionally include other substances to be infused into a dialysate or replacement fluid; non-limiting examples can include glucose, dextrose, acetic acid and citric acid.

An "infusate line" is a fluid connector that connects an infusate container or infusate system to a dialysis flow loop.

The term "infusate system" refers to a component or set of components for adding solutes to a dialysate. The infusate system can comprise an infusate source from which cations or buffer components can be obtained. Examples of cations include, but are not limited to, calcium, magnesium and potassium. Examples of buffer components include, but are not limited to, bicarbonate or acetate. The infusate system can comprise one or more fluid lines, pumps and infusate sources. The infusate source can be a solution containing cations or a dry composition that is hydrated by the system. The infusate system is not limited to cations and may optionally include other substances to be infused into a dialysate or replacement fluid; non-limiting examples can include glucose, dextrose, acetic acid and citric acid.

The term "initiating dialysis" means to begin treatment by dialysis.

An "inlet side of a dialyzer" refers to the side of a dialyzer comprising a fluid inlet. In normal operation, dialysate will enter the dialyzer at the fluid inlet.

The term "intermittently" refers to an action that occurs at intervals, rather than continuously.

An "outlet side of a dialyzer" refers to the side of a dialyzer comprising a fluid outlet. In normal operation, dialysate will exit the dialyzer at the fluid outlet.

The term "passing through" a component refers to the movement of fluid into and out of a component or system.

A "patient" or "subject" is a member of any animal species, preferably a mammalian species, optionally a human. The subject can be an apparently healthy individual, an individual suffering from a disease, or an individual being treated for a disease.

The term "preparing a dialysate" refers to the process of generating a dialysate for use in dialysis from water.

The term "pump" refers to any device that causes the movement of fluids or gases by applying suction or pressure.

The term "regeneration flow loop" refers to a dialysate flow loop comprising one or more components that can prepare dialysate usable in dialysis from spent dialysate. The components can include, but are not limited to, a sorbent cartridge and/or an infusate system.

A "regeneration flow loop pump" is a pump positioned to move fluid through, into or out of a regeneration flow loop.

The term "regeneration mode" refers to a mode of operation of a dialysis system wherein regeneration of a dialysate can take place.

The term "selectively" refers to an action that occurs upon any one or combination of a designated, required, or desired condition.

A "selective dialysate regeneration system" is a dialysis system wherein the dialysate used can be selectively regenerated.

The term "sensor," which can also be referred to as a "detector" in certain instances, as used herein can be a converter that measures a physical quantity of a matter in a solution, liquid or gas, and can convert the physical quantity into a signal which can be read by an electronic instrument.

The terms "sorbent cartridge" and "sorbent container" refer to a cartridge containing one or more sorbent materials for removing specific solutes from solution, such as urea. The term "sorbent cartridge" does not necessarily require the contents in the cartridge be sorbent based. In this connection, the sorbent cartridge may include any suitable amount of one or more sorbent materials. In certain instances, the term "sorbent cartridge" refers to a regeneration cartridge which includes one or more sorbent materials in addition to one or more other regeneration materials. "Sorbent cartridge" includes configurations where at least some of the materials contained in the cartridge do not act by mechanisms of adsorption or absorption.

A "step" is an action, or set of actions, performed during a process.

The term "timing within a dialysis session" refers to a relative point in time during dialysis treatment. The timing within a dialysis session can refer to as a range of time, such as early in a dialysis session; or a specific point of time relative to the dialysis session, such as the initiation of a dialysis session.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

An "ultrafiltrate line" is a fluid connector that connects an ultrafiltration reservoir to a dialysis flow loop.

The term "ultrafiltration reservoir" refers to a container configured to contain ultrafiltrate removed from a subject. In any embodiment, the ultrafiltration reservoir can additionally or alternatively hold dialysate removed from a dialysis flow loop.

"Upstream" refers to the respective positions of two components or positions in a dialysis flow loop. Fluid moving in the dialysis flow loop will contact an upstream component or position prior to contacting a downstream component or position.

A "urea sensor" is a component capable of detecting the presence of, or concentration of urea in a fluid.

A "valve" is a device capable of directing the flow of fluid or gas by opening, closing or obstructing one or more pathways to allow the fluid or gas to travel in a path. One or more valves configured to accomplish a desired flow can be configured into a "valve assembly."

The term "waste solutes" refers to any molecular or ionic species originating from the patient or subject, including metabolic wastes, molecular or ionic species including nitrogen or sulfur atoms, mid-weight uremic wastes and nitrogenous waste. Waste solutes are kept within a specific homeostasis range by individuals with a healthy renal system.

A "water line" is a fluid connector that connects a water source to a dialysis flow loop.

The term "water source" refers to a source from which potable or not potable water can be obtained.

Selective Sorbent Based Regeneration of Dialysate

The first and second aspects of the invention relate to a method and apparatus for performing selective sorbent based regeneration of dialysate. In a selective sorbent based regeneration system, a dialyzer flow loop and a regeneration flow loop are used cooperatively to regenerate spent dialysate during dialysis, thereby reducing the amount of sorbent material needed. FIG. 1 shows an embodiment of a dialysis flow loop for use in selective sorbent based regeneration of dialysate. The selective sorbent based regeneration dialysis flow loop comprises a dialyzer flow loop 101 and a dialysate regeneration flow loop 102. The dialyzer flow loop 101 and regeneration flow loop 102 can be fluidly connected with valves 108 and 109. Valve 108 can control fluid movement from the dialyzer flow loop 101 into the regeneration flow loop 102. Valve 109 can control fluid movement from the regeneration flow loop 102 into the dialyzer flow loop 101.

The dialyzer flow loop 101 can comprise two dialysate storage containers 104 and 105, with a first dialysate storage container 104 located on an inlet side of the dialyzer, and a second dialysate storage container 105 located on the outlet side of the dialyzer. Before initiating dialysis, the dialysate can be initially stored in dialysate storage container 104. During dialysis, dialysate can be moved from the first dialysate storage container 104, through the dialyzer 103 and into the second dialysate storage container 105. At the same time, blood from patient can be circulated through an extracorporeal flow loop (not shown) through the dialyzer 103. Waste solutes in the blood of the patient can pass through the dialyzer membrane and into the dialysate. Initially, the dialysate in dialysate storage container 104 can be fresh dialysate. After passing through the dialyzer 103 and into the second dialysate storage container 105, the dialysate can contain some of the waste solutes that were transferred across the dialyzer membrane.

Once the dialysate initially present in the first dialysate storage container 104 is used in dialysis, the used dialysate in the second dialysate storage container 105 can be selectively moved back into dialysate storage container 104, and the cycle can begin again. Because one pass of dialysate through the dialyzer will not result in a waste solutes concentration in the dialysate that is near the concentration of waste solutes in the patient's blood, the dialysate can be passed through the dialyzer multiple times and can still retain the ability to serve as an effective dialysate.

Dialyzer flow loop pumps 106 and 107 can operate to move dialysate from dialysate storage container 104, through the dialyzer 103 and into dialysate storage container 105. Dialyzer flow loop pump 118 can operate to move dialysate from dialysate storage container 105 back into dialysate storage container 104. Valve 108 can control whether dialysate in dialysate storage container 105 is moved back into dialysate storage container 104, or into the regeneration flow loop 102. In any embodiment of the first or second aspects of the invention, flow sensors (not shown) can be placed on each side of the dialyzer 103. A first flow sensor can be positioned on the inlet side of the dialyzer 103, downstream of dialysate storage container 104. A second flow sensor can be placed on the outlet side of the dialyzer 103, upstream of dialysate storage container 105. The difference in the dialysate flow rate entering the dialyzer and the dialysate flow rate exiting the dialyzer is due to the net fluid removal from the extracorporeal flow path into the dialyzer flow path 101. As such, by positioning a first dialyzer flow loop pump 106 on the inlet side of the dialyzer and a second dialyzer flow loop pump 107 on the outlet side of the dialyzer, the dialyzer flow loop pumps 106 and 107 can be used to accurately control the net ultrafiltrate from the extracorporeal flow loop, which can be monitored by the flow sensors (not shown). The fluid entering dialysate storage container 105 can be a combination of the dialysate and the ultrafiltrate removed from the patient's blood. One skilled in the art will understand that only a single dialyzer flow loop pump can be used, without the same degree of control over ultrafiltration.

After the dialysate has been recirculated through the dialyzer flow loop 101 a number of times, the dialysate can be regenerated by passing the dialysate through regeneration flow loop 102 selectively, or intermittently, based on a desired condition. The regeneration flow loop 102 cooperatively regenerates the dialysate so that the dialysate can be reused in the ongoing dialysis session. In any embodiment of the first or second aspects of the invention, the dialysate can be passed through the regeneration flow loop 102 based on an amount of waste solutes in the dialysate, or any other property of the dialysate or condition of the system. In any embodiment of the first or second aspects of the invention, the amount of waste solutes can be determined by use of an analyte sensor, as described herein. In any embodiment of the first or second aspects of the invention, the amount of waste solutes in the dialysate, and therefore the timing of regeneration of the dialysate, can be estimated based on patient characteristics. In any embodiment of the first or second aspects of the invention, the dialysate can be recirculated through the dialyzer flow loop 101 a set number of times before being regenerated. For example, the dialysate can be recirculated through the dialyzer flow loop 101 2, 3, 4, 5, 6, 7 or more times before regenerating the dialysate. In any embodiment of the first or second aspects of the invention, the dialysate can be recirculated through the dialyzer flow loop a number of times that is based on the concentration of waste solutes in the patient's blood at the start of dialysis, such as the patient's blood urea nitrogen levels (BUN). Patients with a higher BUN will cause the urea concentration in the dialysate to increase at a faster pace than patients with a lower BUN. For patients with a high BUN, the dialysate can be recirculated through the dialyzer flow loop 101 less times before regenerating the dialysate than with patients that have a lower BUN. One of skill in the art will understand that the number of times the dialysate is recirculated through the dialyzer flow loop 101 before regeneration can be determined based on additional or alternative species, such as phosphate levels, sodium levels or any other species in the patient's blood. If the concentration of a particular species in the patient's blood is known before dialysis, one of skill in the art can determine how many times the dialysate can be recirculated through the dialysate flow loop 101 before the dialysate needs to be regenerated to carry on efficient dialysis.

When the dialysate needs to be regenerated, valve 108 can be switched to allow fluid into the regeneration flow loop 102 and into fourth dialysate storage container 120, thereby allowing selective regeneration of the dialysate. When valve 108 is closed to the regeneration flow loop 102, the system is in a dialysis mode, allowing fluid to be recirculated between dialysate storage container 105 and dialysate storage container 104. When valve 108 is open to the regeneration flow loop 102, the system is in a regeneration mode, allowing the dialysate stored in dialysate storage container 105 to enter the regeneration flow loop 102 for regeneration. Dialyzer flow loop pump 118 can be used to move the fluid from dialysate storage container 105 into the regeneration flow loop 102 when the system is in a regeneration mode, and to move the fluid from dialysate storage container 105 to dialysate storage container 104 when the system is in a dialysis mode. In any embodiment of the first or second aspects of the invention, dialyzer flow loop pump 118 can be used only when necessary to regenerate dialysate or to move the fluid in dialysate storage container 105 into dialysate storage container 104 for the purposes of continuing dialysis. In any embodiment of the first or second aspects of the invention, dialyzer flow loop pump 118 can be off during all other times, such that dialyzer flow loop pump 118 essentially acts as a closed valve, keeping the dialysate in dialysate storage container 105. In any embodiment of the first or second aspects of the invention, additional valves can be placed downstream of storage container 105 in order to ensure that no dialysate is moved out of storage container 105 until movement of the dialysate becomes necessary.

Regeneration flow loop 102 can comprise a sorbent cartridge 110. The sorbent cartridge 110 can contain sorbent materials, such as activated carbon, alumina and urease, zirconium phosphate, and zirconium oxide. These sorbent materials can remove waste solutes from the dialysate. The activated carbon in the sorbent cartridge can remove non-ionic waste solutes, such as creatinine, glucose, uric acid, $\beta$2-microglobulin and other non-ionic toxins, except urea. The urease can catalyze the breakdown of urea into ammonia and carbon dioxide, resulting in ammonium carbonate. The alumina can serve as a support for the urease catalyst. The zirconium phosphate can remove the generated ammonium cations, as well as potassium, magnesium, calcium and other cations in the dialysate, replacing these ions with sodium or hydrogen ions originally bound to the zirconium phosphate. The zirconium oxide can remove fluorine, phosphate and other anions from the dialysate, replacing these ions with hydroxide or acetate anions originally bound to the zirconium oxide. In any embodiment of the first or second aspects of the invention, other cation and anion exchange materials can be used in place of the zirconium phosphate and zirconium oxide. One of skill in the art will understand that the sorbent cartridge need not contain every sorbent material listed, and can include less or more sorbent materials depending on the needs of the system. One of skill in the art will also understand that the sorbent materials can be placed in the sorbent cartridge in any order, or can be intermixed within the sorbent cartridge, so long as the cation exchange material is located downstream of the urease.

Because the cation exchange material, such as zirconium phosphate, removes potassium, calcium and magnesium from the dialysate, these ions need to be added back into the dialysate before the dialysate can be used in dialysis. Adding ions or other solutes back into the dialysate can be accomplished by use of an infusate system. Infusate container 114 can contain concentrates or solids of each of the necessary cations. The necessary cations can be added to the regenerated dialysate from infusate container 114 through infusate line 119. In any embodiment of the first or second aspects of the invention, an infusate pump can be located on infusate line 119 to control the movement of the infusates into the regeneration flow loop 102. In any embodiment of the first or second aspects of the invention, the infusates can be located in separate containers (not shown) and need not be present in a single container as illustrated in FIG. 1. In any embodiment of the first or second aspects of the invention, other additives may be added to the regenerated dialysate in the same fashion, such as bicarbonate or acetate buffers.

Fluid moved into the regeneration flow loop can be stored in fourth dialysate storage container 120 for storage prior to regeneration. Once fourth storage container 120 is filled, pump 121 can move the dialysate through the sorbent cartridge 110 and into third dialysate storage container 111. The regenerated dialysate can be moved through the regeneration flow loop into the third dialysate storage container 111 which can serve to store the regenerated dialysate until an entire batch of dialysate is regenerated. Once the entire batch of dialysate is regenerated, the dialysate can be moved by regeneration flow loop pump 112, through valve 109 and back to dialysate storage container 104 to begin the cycle again. The use of two dialysate storage containers in the regeneration flow loop 102 allows both the regeneration flow loop 102 and the dialyzer flow loop 101 to operate simultaneously. The independent operation of the dialyzer flow loop 101 and regeneration flow loop 102 allows for different flow rates in each flow loop that can be individually optimized for each function. The regeneration flow loop flow rate can be optimized to provide the best conditions for regeneration of dialysate, while the dialyzer flow loop flow rate can be optimized to provide the best conditions for removal of solutes from the patient's blood.

In any embodiment of the first or second aspects of the invention, an amount of fluid can be removed from the patient as ultrafiltrate. The ultrafiltrate or spent dialysate can be directed to ultrafiltration reservoir 116 through ultrafiltrate line 117 to remove the ultrafiltrate from the system. In any embodiment of the first or second aspects of the invention, ultrafiltrate reservoir 116 can instead be replaced by a drain or waste container.

The regeneration flow loop 102 shown in FIG. 1 can also be used in preparing the dialysate for use in a dialysis session. Water source 113 can provide water to the regeneration flow loop 102 through water line 115. In any embodiment of the first or second aspects of the invention, a pump may be placed on water line 115 to provide the driving force for moving water from water source 113 into the regeneration flow loop 102. The water can then pass through the sorbent cartridge 110 and receive any necessary infusates from infusate container 114 to generate the initial dialysate. The dialysate can then be moved by regeneration flow loop pump 112, through valve 109 and into dialysate storage container 104 for use in dialysis. Water source 113 can also be used during dialysis whenever additional water is necessary.

In any embodiment of the first or second aspects of the invention, the regeneration flow loop 102 can be utilized while dialysate continues to circulate through the dialyzer flow loop 101. A volume of fluid stored in dialysate storage container 105 can be moved into the regeneration flow loop 102 through valve 108 and the action of pump 118. While dialysate is moved from dialysate storage container 104, through the dialyzer 103 and into dialysate storage container 105, the fluid moved to the regeneration flow loop can be passed through the sorbent cartridge 110, infusates can be added from infusate container 114, and the dialysate can be stored in dialysate storage container 111. After the dialysate in the dialysis flow has been recirculated a set number of times, or otherwise must be regenerated, the regenerated dialysate in dialysate storage container 111 can be moved into dialysate storage 104 container through valve 109 and the action of regeneration flow loop pump 112. This will allow dialysis to continue uninterrupted.

In any embodiment of the first or second aspects of the invention, the valves and pumps described can be controlled by the use of a programmable controller. The controller can be in electronic communication with an analyte sensor, as well as with the pumps and valves described. The controller can determine the correct timing for switching the valves or operating the pumps to move fluid from the dialysate flow loop into the regeneration flow loop, from the regeneration flow loop into the dialysate flow loop, and/or the flow rates in either the dialysate flow loop or the regeneration flow loop. As explained, the controller can cause the valves and pumps to operate to regenerate the dialysate at specific time periods, after a set number of times the dialysate passes through the dialyzer, or in response to the concentration of one or more waste solutes in the dialysate traveling through the dialyzer flow loop.

In any embodiment of the first or second aspects of the invention, one or more analyte sensors can be included in the dialyzer flow loop and/or the regeneration flow loop. In any embodiment of the first or second aspects of the invention, the analyte sensors can include a urea sensor that can sense the concentration of urea or any other solute in the dialyzer flow loop. In any embodiment of the first or second aspects of the invention, the analyte sensor can sense any other waste solutes in the dialysate. In any embodiment of the first or second aspects of the invention, the analyte sensor can be a conductivity sensor. In any embodiment of the first or second aspects of the invention, the analyte sensor can determine the concentration of a waste solutes in the dialysate indirectly, such as by measuring the pH or conductivity of the dialysate. In any embodiment of the first or second aspects of the invention, the dialysate in the dialyzer flow loop can be regenerated based on the amount of waste solutes in the dialysate as determined by data from the analyte sensors. For example, the dialysate in the dialyzer flow loop can be regenerated each time the urea concentration in the dialysate reaches some predetermined level. In any embodiment of the first or second aspects of the invention, the analyte sensors can be unnecessary, and the timing of the regeneration can instead be based on one or more patient parameters, such as the patient's beginning BUN level, as explained. Analyte sensors in the regeneration flow loop can be included to ensure that the regenerated dialysate does not contain any waste products, and has the proper concentrations of solutes for use as a dialysate in dialysis.

In any embodiment of the first or second aspects of the invention, the system can utilize computer models to determine the optimal timing of dialysate regeneration. Once optimal conditions are obtained from computer models, the optimal conditions can be set as profiles. For example, a small number of dialysate recirculation cycles may be optimal during the first 30 minutes of dialysis, followed by disposal of the spent dialysate. Alternatively, using the initial dialysate for several cycles followed by regeneration of the spent dialysate may provide the optimal conditions. Toward the end of the session when concentration levels in the blood are low, the frequency of regeneration may have to increase to maintain overall clearance efficiency and to get the patient to the lowest practical level. One of skill in the art will understand that computer modeling may provide a pragmatic method to determine the timing of dialysate regeneration and the number of cycles through the dialyzer flow loop between regeneration of the dialysate for any point during a dialysis session.

The selective sorbent based regeneration dialysis system illustrated in FIG. 1 allows for increased preservation of the sorbent materials. During traditional sorbent dialysis, potassium, calcium and magnesium are each removed by a cation exchange resin, such as zirconium phosphate, in the sorbent cartridge. Infusates are used to replace these cations in the dialysate so that the dialysate can be recirculated back through the dialyzer. The cation infusates added are then removed by the sorbent cartridge during the next pass of the dialysate through the sorbent cartridge, reducing the functional capacity of the sorbent materials. The system and methods described herein can reduce this effect. Because the dialysate is only circulated through the sorbent cartridge periodically, addition of infusates is only necessary periodically. For example, if the dialysate is circulated through the sorbent cartridge once for every four times the dialysate is circulated through the dialyzer, the infusates necessary will be approximately one quarter of that required if the dialysate was circulated through the sorbent cartridge every time the dialysate was circulated through the dialyzer. Because of the reduced amount of cations added to the dialysate, the sorbent cartridge will remove less cations from the dialysate, thereby preserving the functional capacity of the sorbent, and allowing sorbent dialysis with less of the sorbent materials, thereby reducing size and costs of the sorbent cartridge.

Allowing the dialysate to make multiple passes through the dialyzer before passing through the sorbent cartridge can also result in a lower need for adding bicarbonate or other buffers to the dialysate in order to control for the pH of the dialysate.

In any embodiment of the first or second aspects of the invention, the dialysate can be regenerated at set times. The system can be set to regenerate the dialysate every 1-60 minutes, every 1-20 minutes, every 15-30 minutes, every 20-45 minutes, every 30-40 minutes, every 40-60 minutes or every 40-50 minutes.

In any embodiment of the first or second aspects of the invention, the number of times the dialysate passes through the dialyzer before circulating through the regeneration flow loop, or the amount of time that elapses before recharging the dialysate, can be variable. In any embodiment of the first or second aspects of the invention, the number of passes through the dialyzer can depend on the timing within a dialysis session. For example, the dialysate can be regenerated more frequently at an early point in a dialysis session, when the concentration gradient of waste solutes between the dialysate and the patient's blood is the greatest as opposed to a later point in time of a dialysis session. A higher concentration gradient across the dialyzer membrane will result in more waste solutes entering the dialysate. As such, selective regeneration of the dialysate can occur more often early in a dialysis session in order to remove the increased concentration of waste in the dialysate. In any embodiment of the first or second aspects of the invention, the dialysate can be circulated through the dialyzer flow loop several times at the beginning of a dialysis session, with the selective regeneration of the dialysate beginning in the middle of the dialysis session. In any embodiment of the first or second aspects of the invention, selective regeneration of the dialysate can occur more frequently at a later point of time in a dialysis session, such as towards the end of the dialysis session. Towards the end of a dialysis session the patient waste levels are at their lowest and more frequent regeneration of the dialysate may improve the removal of the low concentration wastes. In any embodiment of the first or second aspects of the invention, the selective regeneration of dialysate may be more frequent in both the early and late stages of the dialysis session, with less frequent regeneration in the middle portion of the dialysis session. In any embodiment of the first or second aspects of the invention, the frequency of dialysate regeneration can be based on the starting uremic level of the patient, wherein selective regeneration of the dialysate occurs more frequently for patients with higher urea blood concentration. In any embodiment of the invention, the frequency of dialysate regeneration can be varied based on a time related algorithm and the starting toxin level of the patient.

In any embodiment of the first or second aspects of the invention, the dialysate can be regenerated less frequently at the beginning of a dialysis session. The dialysate can be circulated through the dialyzer flow loop more times at the beginning of the dialysis session, allowing the waste concentration in the dialysate to approach that of the patient's blood. Later in the dialysis session, when the waste concentration in the patient's blood is lower, the dialysate can be selectively regenerated more frequently, creating a larger concentration and allowing the system to remove the lower concentration waste products from the patient's blood.

In any embodiment of the first or second aspects of the invention, a portion of the spent dialysate can be disposed of and not regenerated. The spent dialysate from near the beginning of a dialysis session will have a higher concentration of waste solutes than the spent dialysate towards the end of a dialysis session. Disposing of a portion of the dialysate from early in the dialysis session will remove this high waste concentration fluid, allowing cooperative regeneration of the later dialysate that will have a lower waste solutes concentration. This can vastly reduce the sorbent material necessary to carry out the dialysis session, as many of the toxin clearance profiles show an exponential decay. That is, the amount of toxins entering the dialysate decreases exponentially throughout a dialysis session. Other toxin clearance profiles show non-exponential decay, such as a linear decay. These toxins also show reduced clearance later in a dialysis session than at the beginning of a dialysis session. Disposing of dialysate from the early portion of a dialysis session, and only regenerating dialysis from later in the dialysis session, may result in 30-50% lower sorbent requirements. In any embodiment of the first or second aspects of the invention, the initial dialysate can be recirculated through the dialyzer flow loop multiple times and then disposed. The initial dialysate can be recirculated through the dialyzer flow loop between any of 1-5, 2-3, 2-4, or 3-5 times before the initial dialysate is disposed.

In any embodiment of the first or second aspects of the invention, the dialysate flow rate through the regeneration flow loop can be a different flow rate than the dialysate flow rate through the dialyzer flow loop. Regeneration of dialysate by passing dialysate through a sorbent cartridge can be more efficient at a lower flow rate. For example, if the dialysate flow rate in the dialyzer flow loop is set at 400 mL/min, the dialysate flow rate in the regeneration flow loop can be set at 100 mL/min, which would allow the dialysate in the dialyzer flow loop to pass through the dialyzer four times while the dialysate in the regeneration flow loop is being regenerated, allowing efficient regeneration of the dialysate. This allows four passes of the dialysate through the dialyzer before regeneration of the dialysate without at pause or gap in the dialysis therapy. One skilled in the art will understand that other flow rates in each of the dialyzer flow loop and regeneration flow loop are possible. In any embodiment of the first or second aspects of the invention, the dialysate flow rate in the dialyzer flow loop can be between any of 1 and 10 times the dialysate flow rate in the regeneration flow loop, between 1 and 2 times the dialysate flow rate in the regeneration flow loop, between 1 and 4 times the dialysate flow rate in the regeneration flow loop, between 2 and 4 times the dialysate flow rate in the regeneration flow loop, between 3 and 5 times the dialysate flow rate in the regeneration flow loop, between 3 and 8 times the dialysate flow rate in the regeneration flow loop, between 5 and 7 times the dialysate flow rate in the regeneration flow loop, or between 7 and 10 times the dialysate flow rate in the regeneration flow loop, depending on how often the dialysate needs to be regenerated.

In any embodiment of the first or second aspects of the invention, the difference in flow rates between the dialyzer flow loop and the regeneration flow loop can vary within a single dialysis session to further enhance the selective and cooperative regeneration of the dialysate. As explained, regeneration of the dialysate more often at the beginning of the dialysis session may be desired. As such, the regeneration flow loop flow rate can be closer to the dialyzer flow loop flow rate at the beginning of a dialysis session, and the flow rate in the regeneration flow loop can be decreased throughout the dialysis session. In any embodiment of the first or second aspects of the invention, regeneration of the dialysate more often near the end of a dialysis session may be desired. As such, the flow rate in the regeneration flow loop may be set closer to the dialyzer flow loop rate near the end of the dialysis session, and further away from the flow rate in the dialyzer flow loop near the beginning of the dialysis session.

In any embodiment of the first or second aspects of the invention, the dialysate storage containers can be of any size. In any embodiment of the first or second aspects of the invention, the size of the dialysate storage containers can be determined based on the desired operating conditions. For example, if the dialyzer flow loop flow rate is set at 400 mL/min, and regeneration of the dialysate is desired to take place every seven minutes with four passes through the dialyzer, the containers will need a volume of (7 min*400 mL/min)/3 containers, or 933 mL/container. In any embodiment of the first or second aspects of the invention, the dialysate storage containers can be sized to hold an entire batch of dialysate. That is, each container can be large enough to hold the dialysate necessary for circulation between instances of regeneration. For example, if the dialyzer flow loop rate is set at 400 mL/min and regeneration of dialysate is desired to take place every seven minutes with four passes through the dialyzer, each container can have a volume of (7 min*400 mL/min) or 2.8 L. If regeneration of the dialysate is desired less often, or if a slower flow rate is desired, smaller containers can be used. If regeneration of the dialysate is desired more often, or a higher flow rate is desired, larger containers can be used. As explained, using a 400 mL/min flow rate in the dialyzer flow loop, and regenerating the dialysate every seven minutes, would require a flow rate in the regeneration flow loop of 933 mL/7 minutes, or 133 mL/min. In any embodiment of the first or second aspects of the invention, the containers can be sized somewhat larger, in order to accommodate an amount of ultrafiltrate removed from the patient. For example, using a 400 mL/min flow rate and regenerating the dialysate every 7 minutes requires containers with volumes of 933 mL. Using 1 L containers would allow for an amount of ultrafiltrate to be removed from the patient and still fit within the containers. In any embodiment of the first or second aspects of the invention, the dialysate storage containers can be between any of 0.5 L to 7 L, 0.5 L to 1 L, 0.5 L to 2 L, 1 L to 2 L, 2 L to 5 L or 5 L to 7 L.

Figure 2:
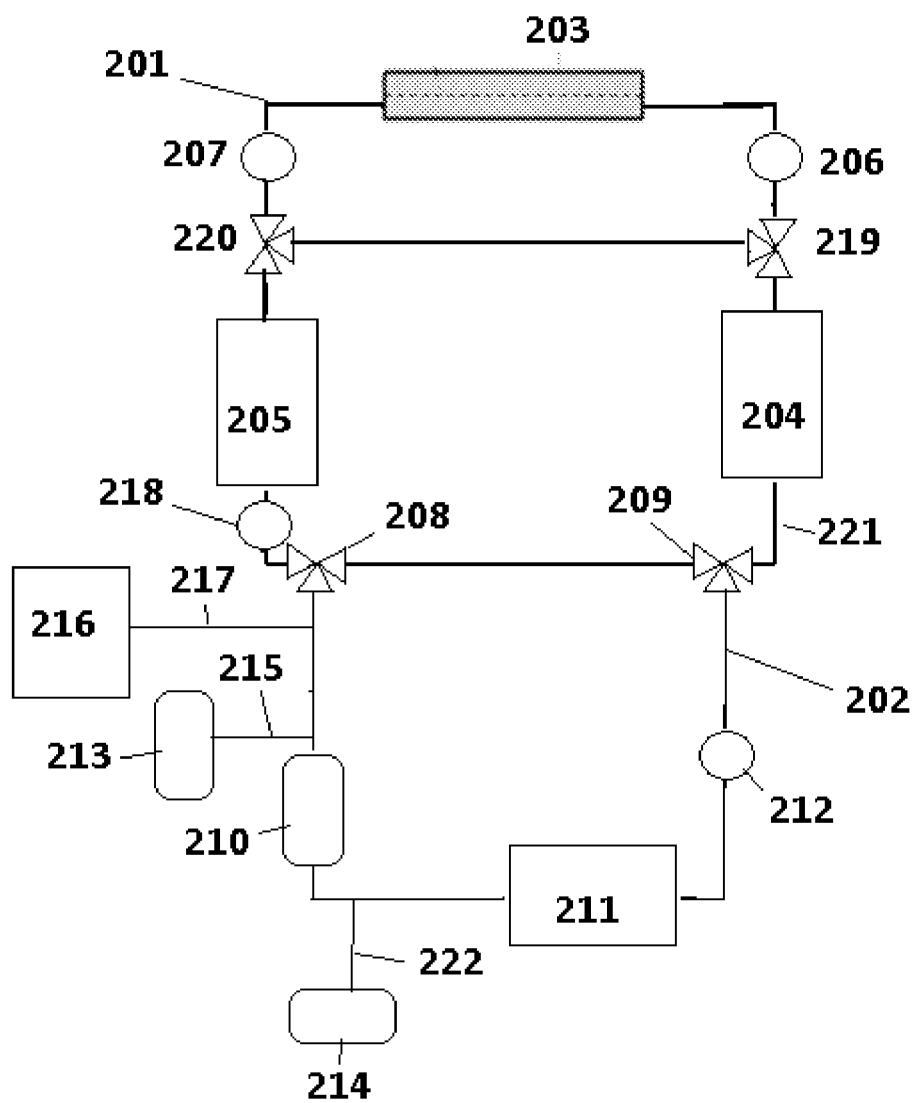
FIG. 2 shows a dialysis flow loop for use in selective sorbent-based regeneration of dialysate utilizing a dialysate storage flow loop.

FIG. 2 shows an embodiment of the first and second aspects of the invention utilizing a separate dialysate storage loop 221. As with the system illustrated in FIG. 1, the system illustrated in FIG. 2 comprises a dialyzer flow loop 201 and a regeneration flow loop 202. The dialyzer flow loop 201 includes dialyzer 203. Dialysate can be recirculated through the dialyzer flow loop 201 with the use of a first dialyzer flow loop pump 206 and/or a second dialyzer flow loop pump 207. As explained, the use of two dialyzer flow loop pumps provides greater control over the rate of ultrafiltration. One skilled in the art will understand that the system can operate with a single dialyzer flow loop pump with less control over ultrafiltration. During dialysis, a first dialyzer flow loop valve 219 and a second dialyzer flow loop valve 220 can be set so that the dialysate circulates through the dialyzer flow loop 201 without entering either the dialysate storage flow loop 221 or the dialysate regeneration flow loop 202.

The dialysate can be recirculated through the dialyzer flow loop 201 until the dialysate is regenerated or discarded. A second portion of fresh dialysate can be held in a first dialysate storage container 204. When the dialysate initially present in the dialyzer flow loop 201 needs to be regenerated or discarded, second dialyzer flow loop valve 220 can be switched to move the dialysate into second storage container 205. First dialyzer flow loop valve 219 can also be switched to move dialysate from the first storage container 204, located in the dialysate storage flow loop 221, into the dialyzer flow loop 201. This allows dialysis to continue using fresh dialysate without the need to stop dialysis for regeneration.

A third portion of dialysate can be present in regeneration flow loop 202. The third portion of dialysate, after creation or regeneration of the third portion of dialysate, can be stored in third dialysate storage container 211. When fresh dialysate is moved from first dialysate storage container 204 into the dialyzer flow loop 201, fresh dialysate from third dialysate storage container 211 can be moved into the first dialysate storage container 204 of the dialysate storage flow loop 221 through third valve 209 by action of regeneration flow loop pump 212. As the dialysate initially present in the third dialysate storage container 211 is moved to the first dialysate storage container 204, spent dialysate present in second dialysate storage container 205 can be moved into the regeneration flow loop 202 through fourth valve 208 by the action of dialysate storage flow loop pump 218. The dialysate moved into the regeneration flow loop 202 can be passed through sorbent cartridge 210 to remove waste species from the dialysate. Infusates can be added to the dialysate from infusate container 214 through infusate line 222 to regenerate the dialysate. The regenerated dialysate can be stored in third dialysate storage container 211 until the dialysate is moved into the dialysate storage flow loop 221. Ultrafiltrate removed from the patient can be directed to ultrafiltration reservoir 216 through ultrafiltrate line 217 to remove the ultrafiltrate from the system. In any embodiment of the first or second aspects of the invention, ultrafiltration reservoir 216 can instead be replaced by a drain.

In any embodiment of the first or second aspects of the invention, as explained, a portion of the spent or used dialysate can be discarded. In any embodiment of the first or second aspects of the invention, the discarded dialysate can be moved to the ultrafiltration reservoir 216, or a drain, through ultrafiltrate line 217. Water source 213 can be used to add water to the system through water line 215. Water can be added to the system to prepare the initial dialysate, as described, or to replace dialysate that has been discarded.

Figure 3:
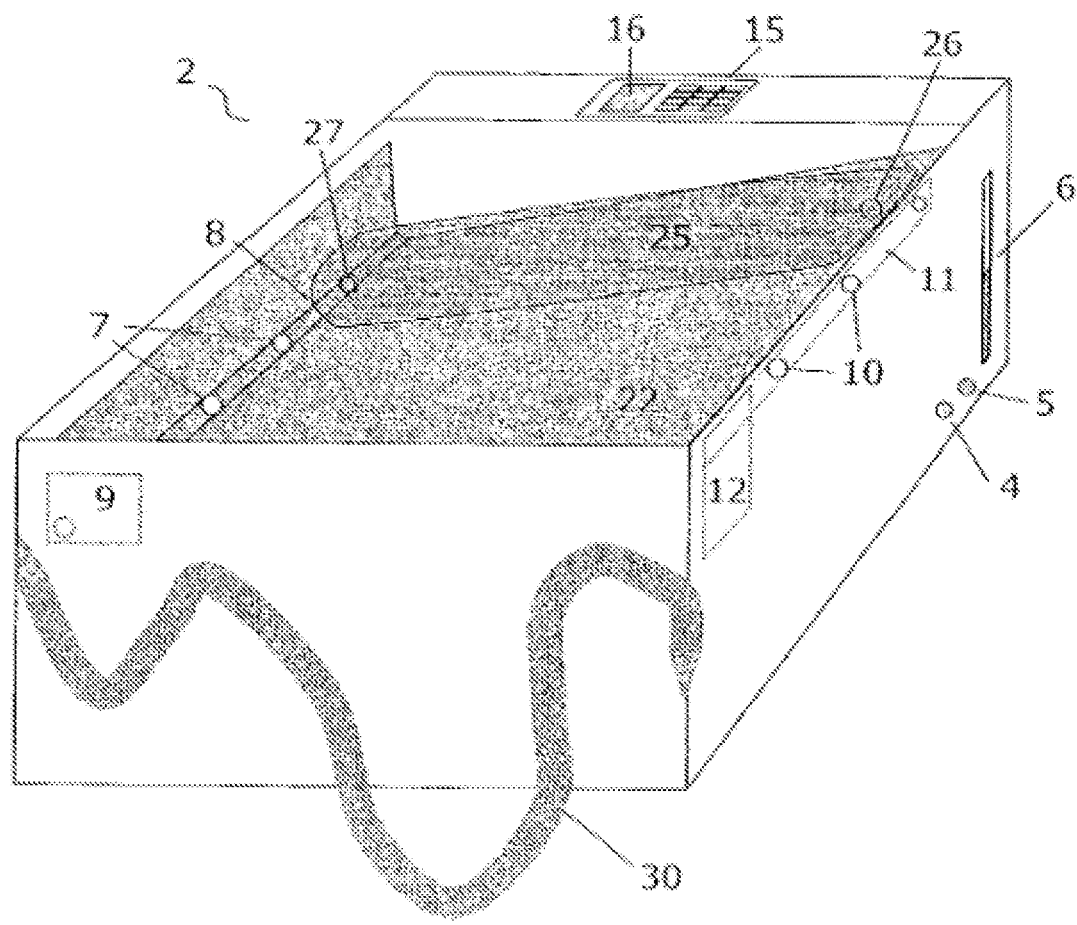
FIG. 3 shows a prior art dialysis system.

A dialysis system allowing for at home dialysis without the need for sorbent materials is described in U.S. Pat. No. 8,034,017 to Peterson, and shown in FIG. 3. The system includes a dialyzer 2, having a blood inlet 4 and outlet 5 for connection to a patient, as well as blood indicator 6. The dialyzer also has dialysate inlet 7 and dialysate outlet 10 connected to inlet pipe 8 and outlet pipe 11. The system also includes two containers, one of which is shown in FIG. 3 as container 25. Pumps 9 and 12 regulate flow into the dialyzer 2 and from the dialyzer into the containers 25. The containers 25 have inlets 26 and outlets 27. The system operates by circulating dialysate from the dialysate containers 25 to the dialyzer 2 and back into the containers. Additional features, such as keypad 15, display 16, or carrying strap 30 can also be included. By reducing the dialysate flow rate, the system can be run using a smaller volume of dialysate. However, a lower flow rate also reduces the flux rate of contaminants across the dialyzer membrane, thereby increasing the necessary dialysis time. The system described is designed for nocturnal home dialysis sessions of 6-8 hours. The system also includes no means to add substances or regulate electrolyte or pH levels during operation. The system also has no sorbent cartridge system to remove contaminants in the dialysate. The operating concept is the 10-20 L starting volume provides enough buffering and dilution capacity throughout the therapy session that the dialysate can be reused because the level of contaminants introduced from the spent dialysis is not significant enough to affect the therapy.

As described, the selective dialysate regeneration system of the present invention eliminates these problems. Because the dialysate is only regenerated selectively, or intermittently, the selective dialysate regeneration system allows for dialysis with a smaller amount of sorbent material and a shorter dialysis time than the described prior art, such as the standard 2-4 hour dialysis sessions. One skilled in the art will understand that the described system can be used for longer than 2-4 hours, as the reduced needs of sorbent materials allows for sorbent dialysis over longer periods of time.

Figure 4A:
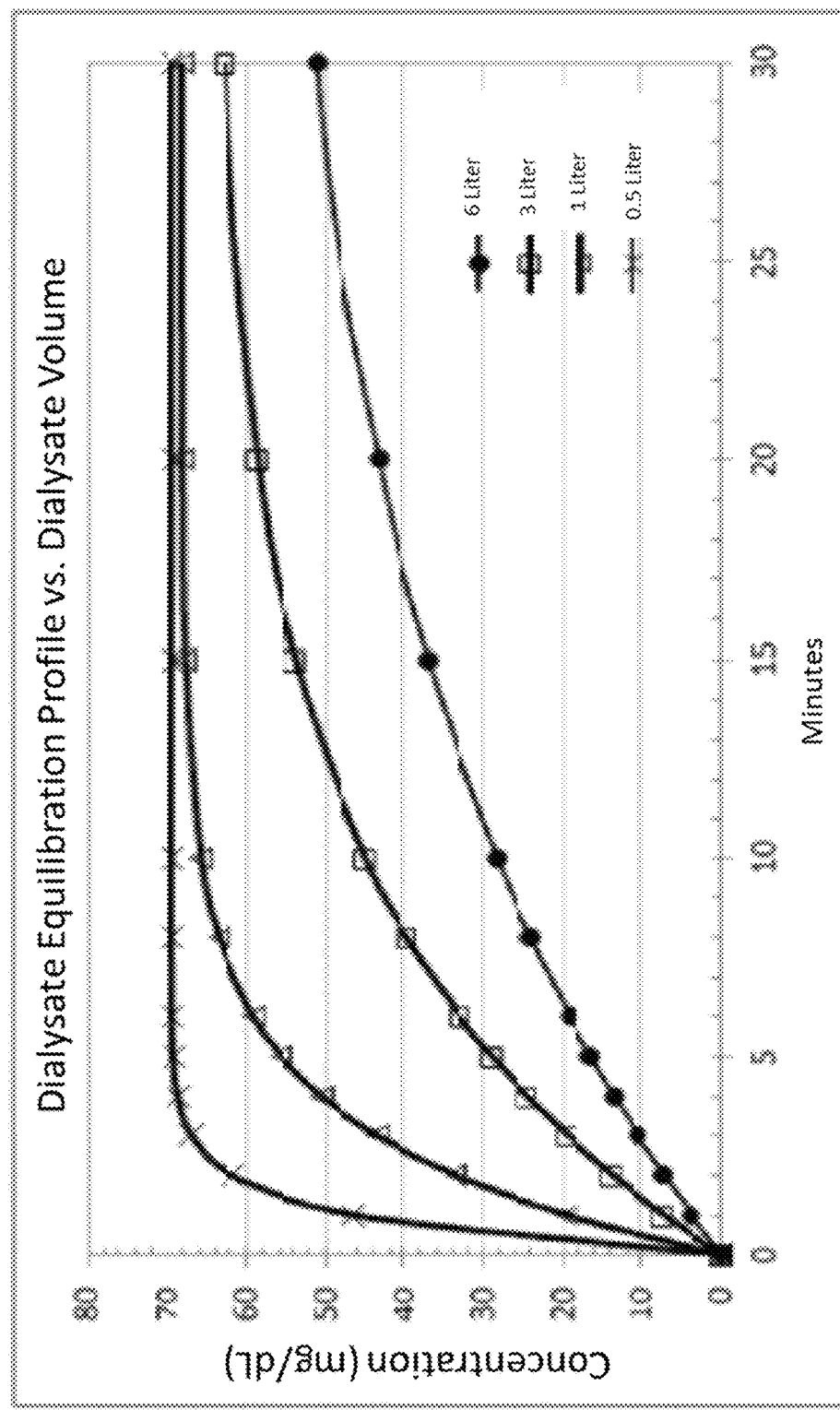
FIG. 4a is a graphical representation of urea concentration in a non-regenerated dialysate over time as a function of dialysate volume.
Figure 4B:
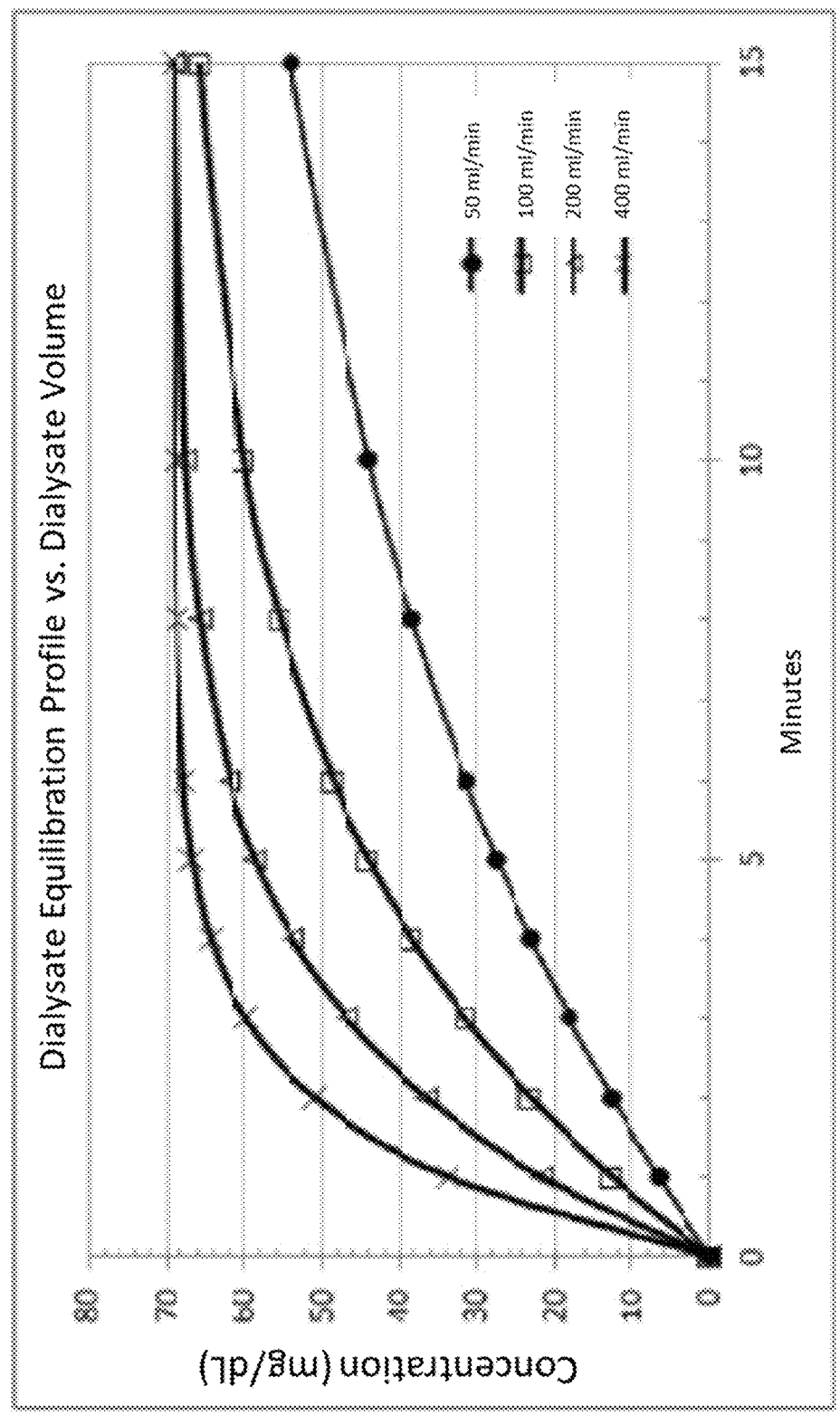
FIG. 4b is a graphical representation of urea concentration in a non-regenerated dialysate over time as a function of dialysate flow rate.

FIG. 4a shows a graphical representation of the effect of dialysate volume on the change in dialysate concentration of urea over time during equilibration with blood at differing dialysate volumes. FIG. 4a illustrates the significant effect dialysate volume has on equilibration time, even at volumes as low as 1 liter. One skilled in the art will understand, based on the data shown in FIG. 4a, that a smaller volume of dialysate in the dialyzer flow loop will require a higher frequency of dialysate regeneration. FIG. 4b shows the effect of dialysate flow rate on the change in dialysate urea concentration over time during equilibration with blood. The data is generated assuming a starting blood urea BUN concentration of 70 mg/dL, a blood flow rate of 400 ml/min, a 1.5 meter square dialyzer and a dialysate volume of 0.5 liters. The dialyzer clearance at dialysate flow rates of 50, 100, 200 and 400 ml/min are assumed to be 50, 100, 190 and 290 ml/min, respectively. FIG. 4b illustrates the significant effect dialysate flow rate has on equilibration time. For example, a dialysate flow rate through the dialyzer flow loop of 100 ml/min requires 15 minutes for equilibration, compared to only 5 minutes required for a dialysate flow rate of 400 ml/min. Therefore, increasing the dialysate flow rate during in the dialyzer flow loop will reduce the time to reach equilibrium and increase the required frequency of regeneration. Likewise, an increase in the rate of blood flow can also increase the dialyzer clearance, K, and thereby decrease the equilibration time. One skilled in the art will understand that the frequency of regeneration of the dialysate can be controlled based on the volume of dialysate in the dialyzer flow loop, the dialysate flow rate through the dialyzer flow loop, and the blood flow rate through the dialyzer.

As shown in FIGS. 4a and 4b, as dialysis progresses without regenerating the dialysate, the concentration of urea in the dialysate will increase until the concentration approaches the patient's blood concentration. At this point, the dialysate will no longer be effective to remove urea from the blood of the patient. In any embodiment of the first or second aspects of the invention, the dialysate in the dialyzer flow loop can be regenerated whenever the urea concentration reaches some level where the dialysate is no longer efficiently removing urea from the patient. For example, the dialysate can be regenerated when the urea concentration in the dialysate reaches 10 mM. As explained, the urea concentration in the dialysate can be determined by one or more analyte sensors, or the urea concentration in the dialysate can be determined mathematically based on the patient's starting BUN levels, the volume of dialysate in the dialyzer flow loop, the dialysate flow rate through the dialyzer flow loop and the blood flow rate through the dialyzer.

Figure 5:
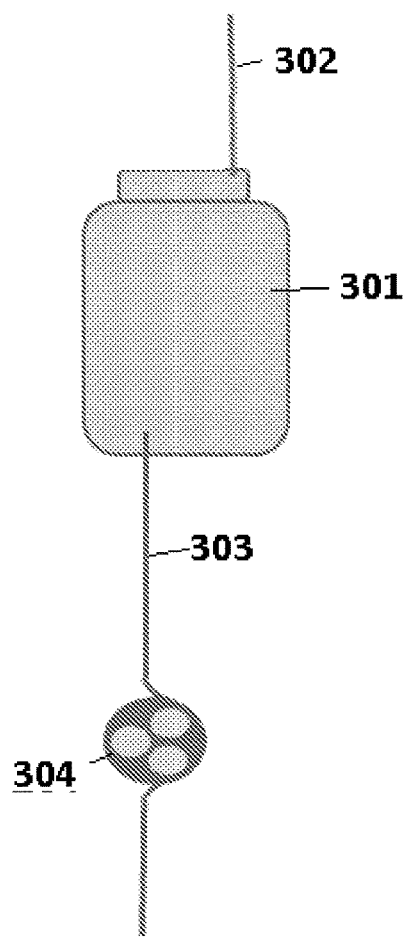
FIG. 5 shows a view of a dialysate storage container for use in a selective sorbent based regeneration system.

FIG. 5 shows an example of a dialysate storage container that can be used in the described selective sorbent based regeneration system. Dialysate can enter the dialysate storage container 301 through fluid connector 302. The dialysate can be stored in dialysate storage container 301 until needed. One skilled in the art will understand that the dialysate storage container 301 can be any of the dialysate storage containers illustrated in FIG. 1. When necessary to remove fluid from the dialysate storage container 301, the dialysate can be drawn out of the bottom of the dialysate storage container 301 through fluid connector 303, by the action of pump 304. In any embodiment of the first or second aspects of the invention, pump 304 can be used only when necessary to move fluid out of dialysate storage container 301, as explained.

Figure 6:
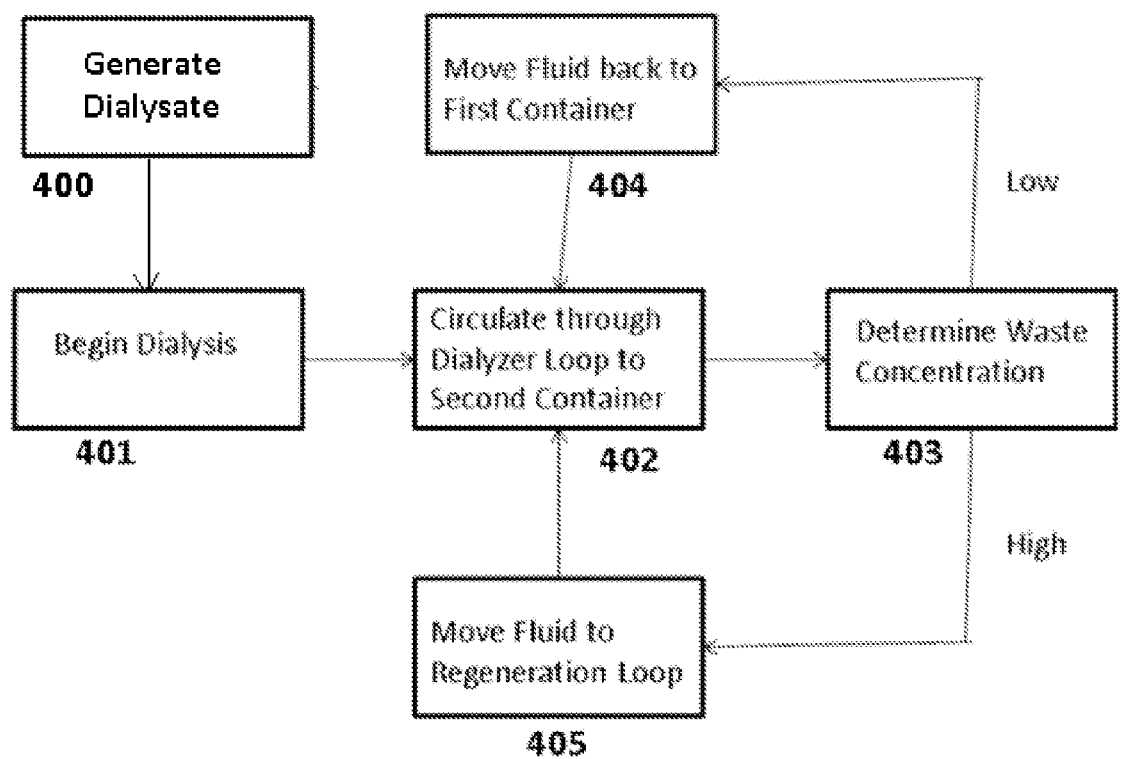
FIG. 6 is a flow chart outlining the process of selective sorbent based regeneration of dialysate.

FIG. 6 shows a flow chart illustrating the selective sorbent based regeneration of dialysate system. At step 400, the initial dialysate can be generated by passing water from a water source through the regeneration flow low, as described. At step 401 dialysis can begin. At step 402, dialysate can be moved from a first dialysate storage container, through the dialyzer, to a second dialysate storage container, as explained with reference to FIG. 1. At step 403, the concentration of waste solutes in the dialysate can be determined. As explained, the concentration of waste solutes in the dialysate can be determined with the use of one or more analyte sensors, or the concentration of waste in the dialysate can be estimated based on the starting conditions of a patient and the time during dialysis. While the concentration of waste solutes in the dialysate remains low, such as below some pre-set point, the dialysate can be moved from the second storage container back to the first storage container in step 404, and dialysis can continue. If the concentration of waste in the dialysate is high, and the dialysate needs to be regenerated, the dialysate in the second dialysate storage container can be transferred to the regeneration flow loop in step 405 as explained to selectively regenerate the dialysate. In any embodiment of the first or second aspects of the invention, dialysate that has been stored in the regeneration flow loop can be moved back to the first container in the dialyzer flow loop to continue dialysis without needing to stop the dialysis session.

Figure 7:
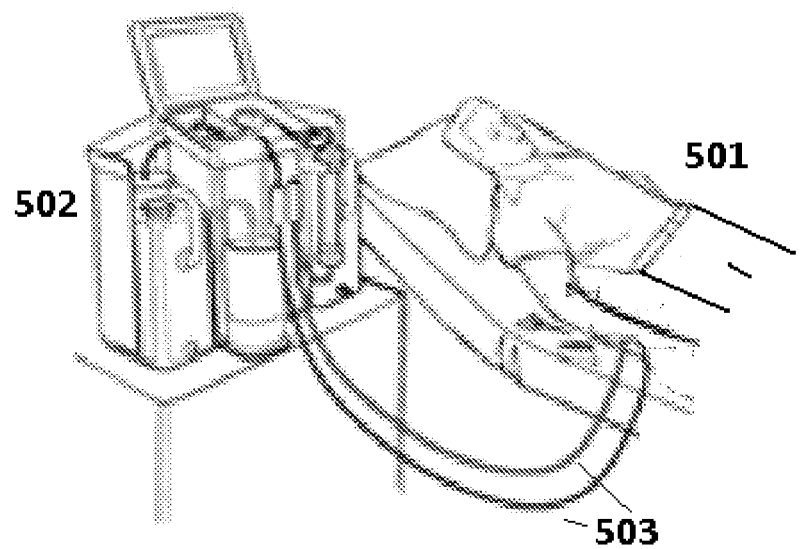
FIG. 7 shows use of a selective sorbent based regeneration system.

The selective dialysate regeneration system is ideal for either home or clinical use. As shown in FIG. 7, a patient 501 can be connected to the selective dialysate regeneration system 502 by fluid connectors 503, which in any embodiment of the first or second aspects of the invention can be lengths of tubing. Because of the lower requirements on sorbent materials as compared to traditional sorbent dialysis systems, the selective dialysate regeneration system allows for lower cost treatment, as in most cases the savings from the decrease in amount of sorbent material used more than offsets the slightly increased need for clean water. Further, because the dialysate is regenerated as necessary, the selective dialysate regeneration system allows for a faster dialysate flow rate than the prior art, thereby increasing the flux rate of contaminants across the dialyzer and decreasing the necessary patient treatment time. Additionally, because the selective dialysate regeneration system requires less sorbent material per unit time as compared to other sorbent dialysis systems, the selective dialysate regeneration system allows for overnight use by a patient in a clinic or at home, which would not be possible with traditional sorbent based systems that regenerate dialysate after each pass through the dialyzer.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

I claim:
1. A dialysis flow loop, comprising:
a dialyzer flow loop having a dialyzer and at least a first dialysate storage container;
a regeneration flow loop having a sorbent cartridge, the regeneration flow loop fluidly connectable to the dialyzer flow loop;
at least one valve positioned to control fluid movement between the dialyzer flow loop and the regeneration flow loop;
an analyte sensor positioned in the dialyzer flow loop, the analyte sensor in electronic communication with the controller; and
the controller to control the valve, wherein the controller is programmed to control the valve based on an amount of waste solutes in a dialysate in the dialyzer flow loop.

2. The dialysis flow loop of claim 1, further comprising at least a first dialyzer flow loop pump located in the dialyzer flow loop, and at least one regeneration flow loop pump located in the regeneration flow loop.

3. The dialysis flow loop of claim 2, further comprising a second dialyzer flow loop pump, wherein the first dialyzer flow loop pump is located on an inlet side of the dialyzer, and wherein the second dialyzer flow loop pump is located on an outlet side of the dialyzer.

4. The dialysis flow loop of claim 1, further comprising a second dialysate storage container in the dialyzer flow loop; wherein the first dialysate storage container is located on an inlet side of the dialyzer, and wherein the second dialysate storage container is located on an outlet side of the dialyzer.

5. The dialysis flow loop of claim 4, wherein fluid exiting the dialyzer enters the second dialysate storage container.

6. The dialysis flow loop of claim 4, wherein fluid exiting the first dialysate storage container enters the dialyzer.

7. The dialysis flow loop of claim 4, wherein one or both of the dialysate storage containers have a volume of between any of 0.5 L to 7 L, 0.5 L to 1 L, 0.5 L to 2 L, 1 L to 2 L, 2 L to 5 L or 5 L to 7 L.

8. The dialysis flow loop of claim 4, further comprising a first flow sensor on the inlet side of the dialyzer and downstream of the first dialysate storage container, and a second flow sensor on the outlet side of the dialyzer and upstream of the second dialysate storage container.

9. The dialysis flow loop of claim 8, further comprising a first dialyzer flow loop pump located on the inlet side of the dialyzer downstream of the first dialysate storage container; and a second dialyzer flow loop pump located on the outlet side of the dialyzer upstream of the second dialysate storage container.

10. The dialysis flow loop of claim 1, further comprising a dialysate storage container in the regeneration flow loop at a position downstream of the sorbent cartridge.

11. The dialysis flow loop of claim 1, wherein the controller switches the valve between a dialysis mode and a regeneration mode, wherein fluid does not enter the regeneration flow loop from the dialyzer flow loop in the dialysis mode, and wherein fluid enters the regeneration flow loop from the dialyzer flow loop in the regeneration mode.

12. The dialysis flow loop of claim 1, wherein the regeneration flow loop further comprises an infusate system.

13. The dialysis flow loop of 1, wherein the analyte sensor is a urea sensor or a conductivity sensor.

14. The system of claim 1, wherein the controller is programmed to control the valve to move dialysate to the regeneration loop when the waste species concentration in the dialysate reaches a predetermined level.

15. A method, comprising:
    initiating dialysis with dialysate initially located in a first dialysate storage container positioned in a dialyzer flow loop;
    passing the dialysate through a dialyzer and into a second dialysate storage container positioned in the dialyzer flow loop; and
    moving the dialysate in the second dialysate storage container into the first dialysate storage container;
    measuring a concentration of a waste species in the dialysate with an analyte sensor located in the dialyzer flow loop and communicating the concentration of the waste species to a controller;
    selectively moving the dialysate from the second dialysate storage container into a regeneration flow loop based on an amount of waste species in the dialysate by the controller, wherein the regeneration flow loop comprises a sorbent cartridge; passing the dialysate through the sorbent cartridge to create a regenerated dialysate, and then moving the regenerated dialysate from the regeneration flow loop to the first storage container.

16. The method of claim 15, wherein the dialysate is moved from the second storage container to the first storage container when the first storage container is empty.

17. The method of claim 15, wherein the regenerated dialysate is stored in a third dialysate storage container prior to moving the regenerated dialysate to the first dialysate storage container.

18. The method of claim 17, wherein the regenerated dialysate is stored in the third dialysate storage container for less than one hour prior to moving the regenerated dialysate to the first storage container.

19. The method of claim 15, wherein the amount of dialysate initially present in the first dialysate storage container is between any of 0.5 L to 7 L, 0.5 L to 1 L, 0.5 L to 2 L, 1 L to 2 L, 2 L to 5 L or 5 L to 7 L.

20. The method of claim 15, further comprising the step of preparing a dialysate prior to initiating the dialysis session; wherein preparing the dialysate comprises:
    moving water from a water source into the regeneration flow loop;
    passing the water through the sorbent cartridge;
    adding one or more infusates to the water to create a dialysate; and
    moving the dialysate from the regeneration flow loop into the first storage container.

21. The method of claim 15, wherein the dialysate is moved from the second dialysate storage container into the regeneration flow loop any of every 1-60 minutes, every 1-20 minutes, every 1-7 minutes, every 5-10 minutes, every 7-12 minutes, every 5-15 minutes, every 10-15 minutes, every 12-20 minutes, every 15-30 minutes, every 20-45 minutes, every 30-40 minutes, every 40-60 minutes or every 40-50 minutes.

22. The method of claim 15, wherein a second volume of dialysate is moved from a third dialysate storage container positioned in the regeneration flow loop to the first dialysate storage container when dialysate from the second storage container is moved to the regeneration flow loop.

23. The method of claim 22, wherein a flow rate of dialysate in the dialyzer flow loop is faster than a flow rate of dialysate in the regeneration flow loop.

24. The method of claim 23, wherein the flow rate of dialysate in the dialyzer flow loop is between any of 1-10, 1-2, 1-4, 2-4, 3-5, 3-8, 5-7, or 7-10 times the flow rate of dialysate in the regeneration flow loop.

25. The method of claim 15, wherein dialysate is moved into the regeneration flow loop based on a timing within a dialysis session.

26. The method of claim 25, wherein dialysate is moved into the regeneration flow loop more frequently at a later point in the dialysis session than at an earlier point in the dialysis session.

27. The method of claim 25, wherein the dialysate initially located in the first dialysate storage container is disposed of and is not regenerated.

28. The method of claim 15, further comprising the step of moving the dialysate to the regeneration flow loop when the concentration of the waste species reaches a predetermined level.

* * * * *